(12) United States Patent
    Allen

(10) Patent No.: US 9,757,489 B2
(45) Date of Patent: Sep. 12, 2017

(54) SYSTEM AND METHOD FOR MODULAR COMPONENT STERILIZATION CASE

(75) Inventor: Kraig Herman Allen, Warsaw, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 1926 days.

(21) Appl. No.: 12/326,331

(22) Filed: Dec. 2, 2008

(65) Prior Publication Data

US 2009/0223972 A1    Sep. 10, 2009

Related U.S. Application Data

(60) Provisional application No. 61/033,557, filed on Mar. 4, 2008.

(51) Int. Cl.
| | |
|---|---|
| *B65D 6/00* | (2006.01) |
| *B65D 8/14* | (2006.01) |
| *B65D 6/28* | (2006.01) |
| *B65D 8/04* | (2006.01) |
| *B65D 8/06* | (2006.01) |
| *B65D 83/10* | (2006.01) |
| *A61B 50/33* | (2016.01) |
| *B65D 6/26* | (2006.01) |
| *B65D 6/24* | (2006.01) |
| *A61L 2/26* | (2006.01) |
| *A61B 50/30* | (2016.01) |
| *A61B 50/00* | (2016.01) |

(52) U.S. Cl.
CPC ............... *A61L 2/26* (2013.01); *A61B 50/30* (2016.02); *A61B 2050/006* (2016.02); *A61L 2202/122* (2013.01); *A61L 2202/182* (2013.01); *A61L 2202/24* (2013.01)

(58) Field of Classification Search
CPC .. B65D 7/32; B65D 11/1866; B65D 11/1873; Y10T 403/342; A61L 2202/23; A61L 2202/24; A61B 50/33
USPC ............ 220/4.33, 4.34, 622, 692, 693, 4.28; 206/438, 363, 370
See application file for complete search history.

(56) References Cited

U.S. PATENT DOCUMENTS

| | | | | |
|---|---|---|---|---|
| 3,315,639 | A * | 4/1967 | Close | 118/642 |
| 3,659,389 | A * | 5/1972 | Forberg | 52/285.3 |
| 4,757,909 | A * | 7/1988 | Matsuura | 220/7 |
| 5,004,116 | A * | 4/1991 | Cattarozzi | 220/4.34 |
| 5,367,742 | A * | 11/1994 | Bindman | 16/87.2 |
| 6,390,359 | B1 * | 5/2002 | Lin | 229/198 |
| 6,631,821 | B2 * | 10/2003 | Vourganas | 220/1.5 |
| 6,749,077 | B1 * | 6/2004 | McAlpine et al. | 220/4.29 |
| 2002/0071799 | A1 | 6/2002 | Wood | |
| 2005/0238530 | A1 | 10/2005 | Frieze et al. | |

\* cited by examiner

*Primary Examiner* — Andrew T Kirsch
(74) *Attorney, Agent, or Firm* — Hayes Soloway PC

(57) ABSTRACT

A modular component container system includes a plurality of case walls and a plurality of connectors. Each of the connectors includes at least two connector elements that mechanically connect to the case walls. The system also includes at least one latch connector having a latch connector element. The latch connector element mechanically connects to one of the case walls. A latch is movably oriented relative to the latch connector element. The latch releasably engages another of the case walls.

11 Claims, 8 Drawing Sheets

SYSTEM AND METHOD FOR MODULAR COMPONENT STERILIZATION CASE

CROSS REFERENCE TO RELATED APPLICATION

This application claims benefit of U.S. Provisional Application Ser. No. 61/033,557 filed Mar. 4, 2008, the entire disclosure of which is incorporated herein by reference.

FIELD OF THE INVENTION

The present invention is generally related to sterilization cases and more particularly is related to modular component sterilization cases.

BACKGROUND OF THE INVENTION

Sterilization cases are used in the medical field to hold medical instruments. The medical instruments, when contaminated, are run through a sterilizer while held within a sterilization case. Sterilization cases, and containers in general, when purchased remotely and shipped are generally shipped inefficiently. More specifically, many containers, including sterilization cases, are shipped assembled and occupy significantly more space during shipping than would be required if the containers could be shipped unassembled.

Thus, a heretofore unaddressed need exists in the industry to address the aforementioned deficiencies and inadequacies.

SUMMARY OF THE INVENTION

Embodiments of the present invention provide a system and method for utilizing a modular component sterilization system. Briefly described, in architecture, one embodiment of the system, among others, can be implemented as follows. The modular component sterilization system includes a plurality of case walls and a plurality of connectors. Each of the connectors includes at least two connector elements that mechanically connect to the case walls. The modular component sterilization system also includes at least one latch connector having a latch connector element. The latch connector element mechanically connects to one of the case walls. A latch is movably oriented relative to the latch connector element. The latch releasably engages another of the case walls.

The present invention can also be viewed as providing methods for assembling a modular component sterilization case. In this regard, one embodiment of such a method, among others, can be broadly summarized by the following steps: connecting a plurality of case walls using a plurality of connectors to form a container, wherein each of the connectors includes at least two connector elements that mechanically connect to the case walls; and removably latching one of the case walls to the container using at least one latch connector having a latch connector element that mechanically connects to one of the case walls and a latch movably oriented with the latch connector element, wherein the latch releasably engages another of the case walls, whereby the removably latched case wall is operably a cover for the container.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
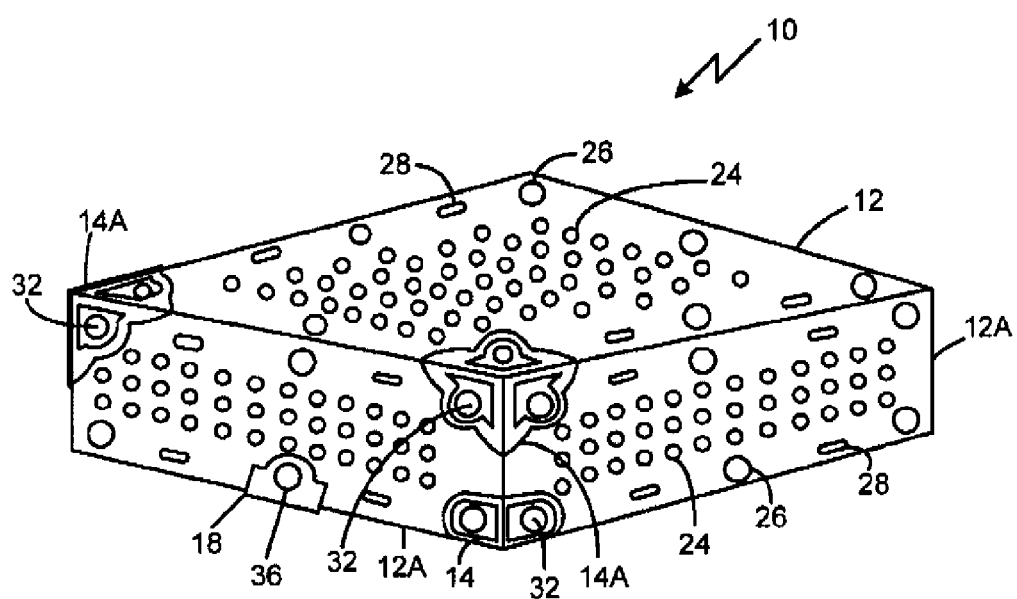
FIG. 1 is a perspective illustration of an assembled modular component sterilization system, in accordance with a first exemplary embodiment of the present invention.

FIG. 1 is a perspective illustration of an assembled modular component sterilization system 10, in accordance with a first exemplary embodiment of the present invention. The system 10 contains a plurality of case walls 12, 12A and a plurality of connectors 14, 14A. Each of the connectors 14, 14A includes at least two connector elements 16 that mechanically connect to the case walls 12, 12A. The system 10 also includes at least one latch connector 18. The latch connector 18 includes at least one latch connector element 36 that mechanically connects to one of the case walls 12, 12A. A latch 46 is movably oriented relative to the latch connector element 36. The latch 46 releasably engages another of the case walls 12, 12A.

The modular component sterilization system 10 may be shipped in pieces and assembled by the consumer. The pieces of the modular component sterilization system 10 may be sufficiently rugged so as to withstand repeated exposure to a sterilization environment as well as sharp medical instruments. The modular component sterilization system 10 may be substantially disassembled to allow sterilization of the modular component sterilization system 10 without leaving crevices to collect residual contaminants.

While FIG. 1 shows the case walls 12, 12A abutting, the modular component sterilization system 10 may be designed to leave a gap along the edges at which case walls 12, 12A proximately meet. As the modular component sterilization system 10 may be designed to be liquid permeable, and is illustrated as being liquid permeable, leaving intended gaps at these edges will not be detrimental to the performance of the modular component sterilization system 10.

Figure 2:
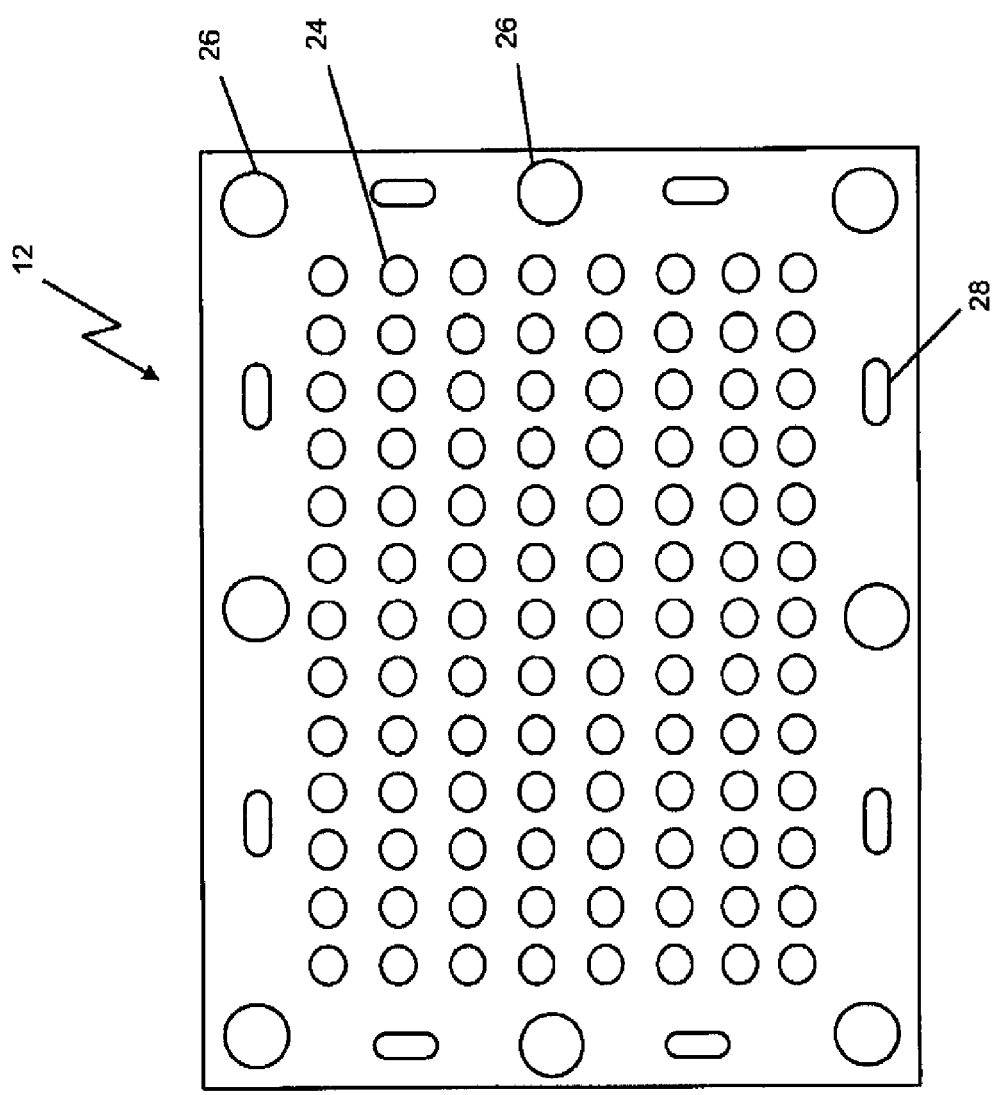
FIG. 2 is a top view of one of the case walls of the modular component sterilization system shown in FIG. 1, in accordance with the first exemplary embodiment of the present invention.

FIG. 2 is a top view of one of the case walls 12 of the modular component sterilization system 10 shown in FIG. 1, in accordance with the first exemplary embodiment of the present invention. The case wall 12 has a plurality of holes 24 through which sterilizing fluids, including gases, may pass to sterilize the contents of the modular component sterilization system 10. Along a perimeter of the case wall 12 are openings 26 and slots 28. The openings 26 and slots 28 may be used to receive the connectors 14, 14A (shown in FIG. 1) and/or latch connectors 18 (shown in FIG. 1). One skilled in the art will recognize there are other structures and shapes for the holes 24 of the case wall 12 that may be adopted to allow sterilizing fluids and gases to effectively pass through the modular component sterilization system 10 shown in FIG. 1, and all such structures and shapes are considered to be within the scope of the present invention. Similarly the openings 26 and slots 28 may be sized and/or shaped differently and may be sized identical to the holes 24 without deviating from the scope of the present invention.

Figure 3:
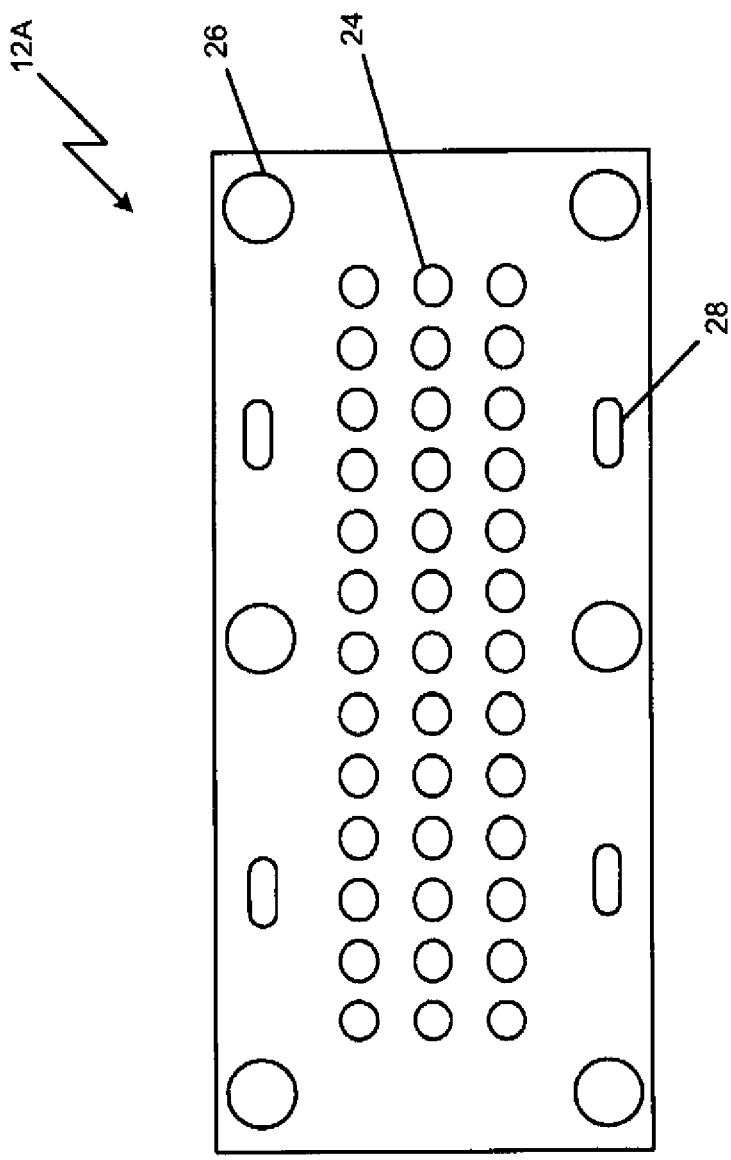
FIG. 3 is a top view of another one of the case walls of the modular component sterilization system shown in FIG. 1, in accordance with the first exemplary embodiment of the present invention.

FIG. 3 is a top view of another one of the case walls 12A of the modular component sterilization system 10 shown in FIG. 1, in accordance with the first exemplary embodiment of the present invention. The case wall 12A has a plurality of holes 24 through which sterilizing fluids, including gases, may pass to sterilize the contents of the modular component sterilization system 10. Along a perimeter of the case wall 12A are openings 26 and slots 28. The openings 26 and slots 28 may be used to receive the connectors 14, 14A (shown in FIG. 1) and/or latch connectors 18 (shown in FIG. 1). While only two sizes of case walls 12, 12A are shown in this disclosure, one of ordinary skill in the art will recognize innumerable sizes and shapes of case walls 12, 12A, including sizes and shapes that provide greater or fewer than six sides to the modular component sterilization system 10 are conceivable and considered to be within the scope of the present invention.

Figure 4:
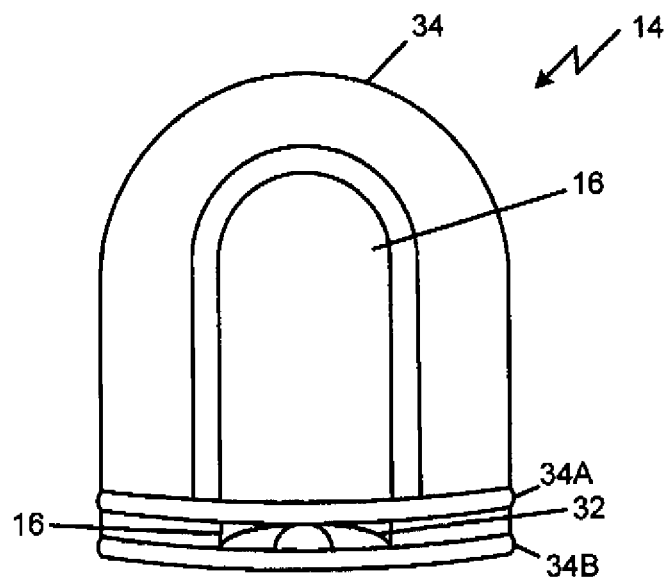
FIG. 4 is a front view of a first exemplary connector of the modular component sterilization system shown in FIG. 1, in accordance with the first exemplary embodiment of the present invention.
Figure 5:
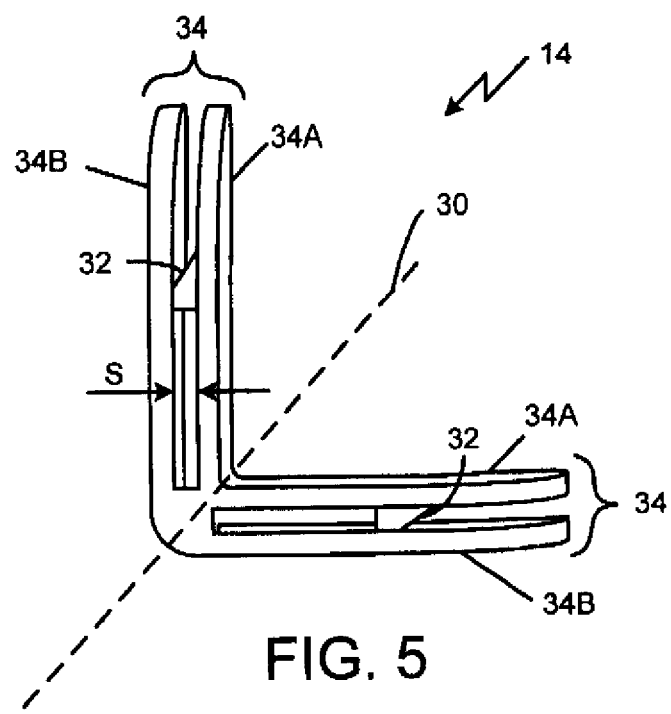
FIG. 5 is a side view of the first exemplary connector shown in FIG. 4, in accordance with the first exemplary embodiment of the present invention.

FIG. 4 is a front view of a first exemplary connector 14 of the modular component sterilization system 10 shown in FIG. 1, in accordance with the first exemplary embodiment of the present invention. FIG. 5 is a side view of the first exemplary connector 14 shown in FIG. 4, in accordance with the first exemplary embodiment of the present invention. The connector 14 may be symmetrical across a first axis 30, as shown in FIG. 5. The connector 14 may have two connector elements 16. The connector elements 16 may be flexible tabs having cylindrical protrusions 32. The cylindrical protrusions 32 may be sized to be received by the openings 26 and/or slots 28 of the case walls 12, 12A shown in FIG. 2 and FIG. 3. The connector 14 may also include at least one pair of bracing elements 34. The pair of bracing elements 34 may be substantially parallel, as shown in FIG. 5, and spaced a distance S exceeding a thickness of the case walls 12, 12A (shown in FIG. 2 and FIG. 3). The bracing elements 34 may be located about a periphery of the connector elements 16. The connector element 16 may be coplanar with a first bracing element 34A of the pair of bracing elements 34 and the cylindrical protrusion 32 may extend from the connector element 16 toward the second bracing element 34B of the pair of bracing elements 34.

Operationally, a case wall 12, 12A may be slid between the pair of bracing elements 34 so that the cylindrical protrusion 32 contacts the case wall 12, 12A and the connector element 16 flexes away from the second bracing element 34B. The flexing of the connector element 16 allows the case wall 12, 12A to slide further between the pair of bracing elements 34 such that the cylindrical protrusion 32 on the connector element 16 engages with the openings 26 and/or slots 28. The cylindrical protrusion 32 may be beveled to further enable the connector element 16 to flex away from the second bracing element 34B on contact from the case wall 12, 12A, but limit flexing when a pulling force is exerted between the connector 14 and the case wall 12, 12A. To remove the case wall 12, 12A, the protrusion 32 may be pushed from the opening 26 and/or slots 28 to disengage the connector element 16. As shown in FIG. 5, the connector 14 may include two pairs of bracing elements 34 oriented at an approximate right angle, thereby allowing the case walls 12, 12A connected to the connector 14 to be mounted at an approximate right angle.

Figure 6:
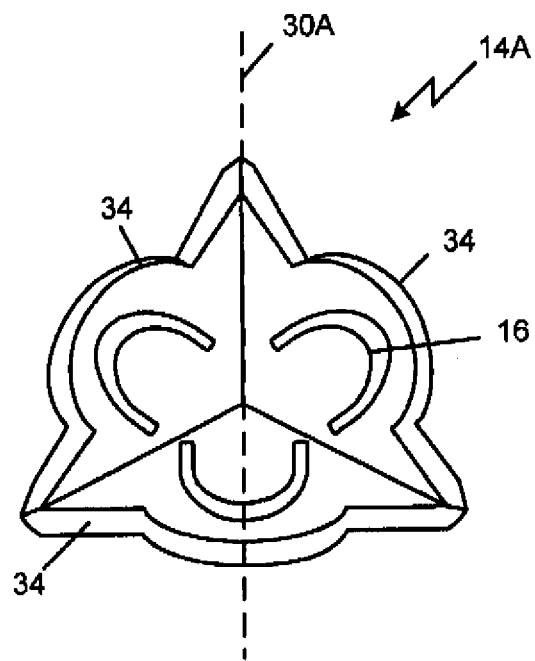
FIG. 6 is a front view of an exemplary corner connector of the modular component sterilization system shown in FIG. 1, in accordance with the first exemplary embodiment of the present invention.
Figure 7:
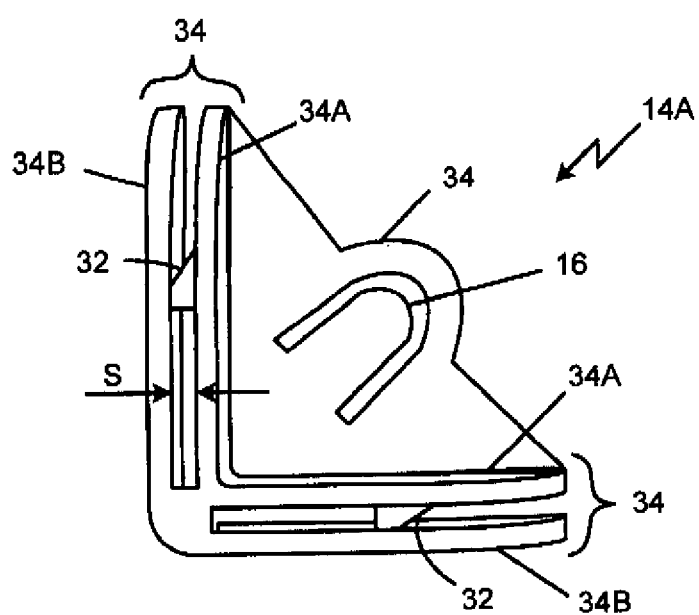
FIG. 7 is a side view of the exemplary corner connector shown in FIG. 6, in accordance with the first exemplary embodiment of the present invention.

FIG. 6 is a front view of an exemplary corner connector 14A of the modular component sterilization system 10 shown in FIG. 1, in accordance with the first exemplary embodiment of the present invention. FIG. 7 is a side view of the exemplary corner connector 14A shown in FIG. 6, in accordance with the first exemplary embodiment of the present invention. The corner connector 14A may be symmetrical across a first axis 30A, as shown in FIG. 6. The corner connector 14A may have three connector elements 16. The connector elements 16 may be flexible tabs having cylindrical protrusions 32. The cylindrical protrusions 32 may be sized to be received by the openings 26 and/or slots 28 of the case walls 12, 12A shown in FIG. 2 and FIG. 3. The corner connector 14A may also include three pair of bracing elements 34. The pair of bracing elements 34 may be substantially parallel, as shown in FIG. 7, and spaced a distance S exceeding a thickness of the case walls 12, 12A (shown in FIG. 2 and FIG. 3). The bracing elements 34 may be located about a periphery of the connector elements 16. The connector element 16 may be coplanar with a first bracing element 34A of the pair of bracing elements 34 and the cylindrical protrusion 32 may extend from the connector element 16 toward the second bracing element 34B of the pair of bracing elements 34.

Operationally, a case wall 12, 12A may be slid between the pair of bracing elements 34 so that the protrusion 32 contacts the case wall 12, 12A and the connector element 16 flexes away from the second bracing element 34B. The flexing of the connector element 16 allows the case wall 12, 12A to slide further between the pair of bracing elements 34 such that the protrusion 32 on the connector element 16 engages with the openings 26 and/or slots 28. The protrusion 32 may be beveled to further enable the connector element 16 to flex away from the second bracing element 34B on contact from the case wall 12, 12A, but limit flexing when a pulling force is exerted between the connector 14 and the case wall 12, 12A. To remove the case wall 12, 12A, the protrusion 32 may be pushed from the opening 26 and/or slots 28 to disengage the connector element 16.

Figure 8:
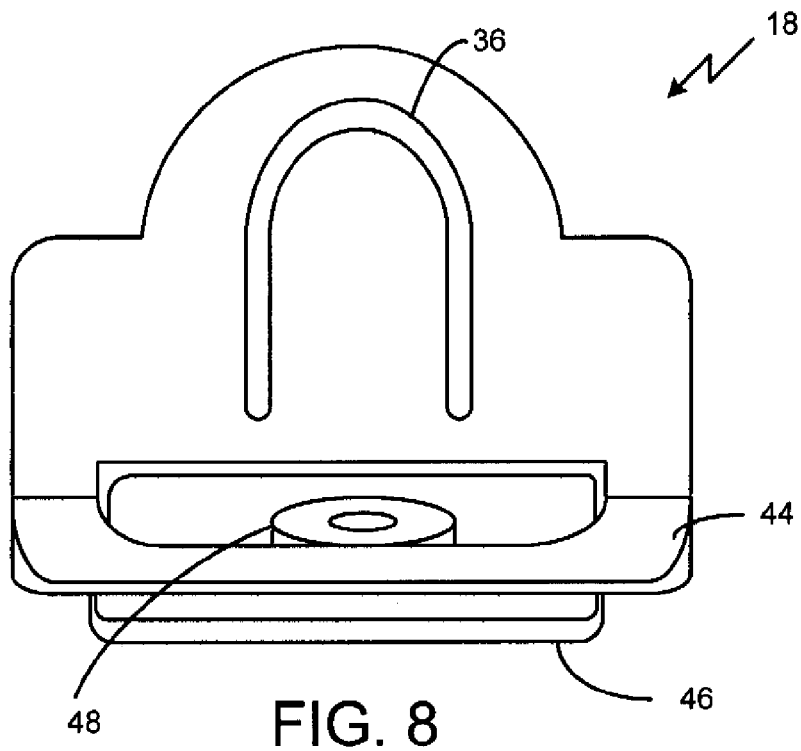
FIG. 8 is a front view of a first exemplary latch connector for the modular component sterilization system shown in FIG. 1, in accordance with the first exemplary embodiment of the present invention.
Figure 9:
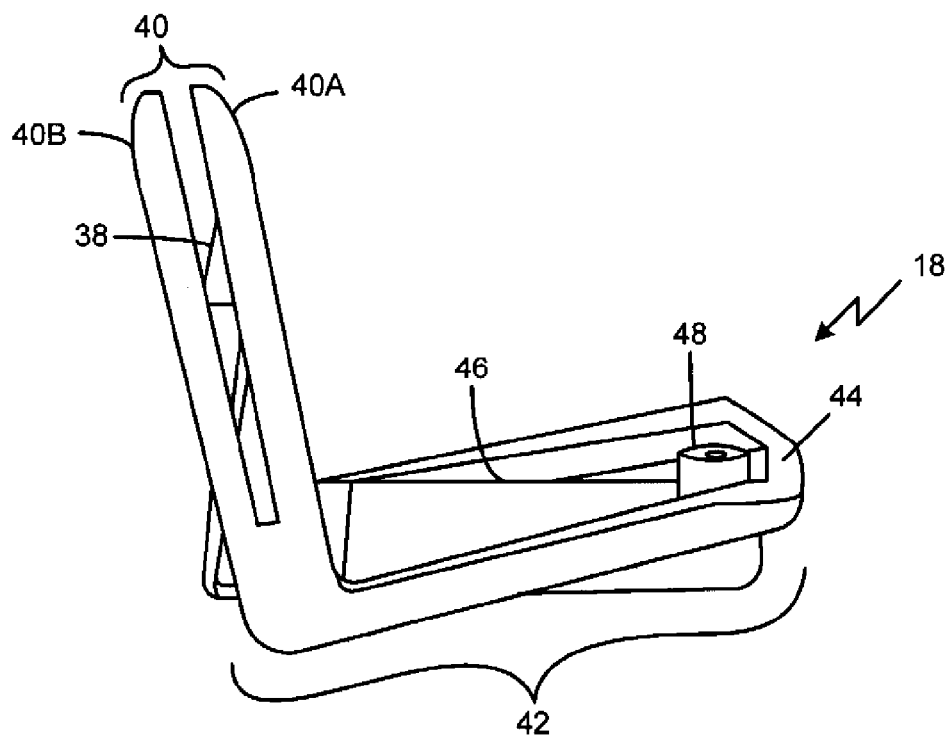
FIG. 9 is a side view of the first exemplary latch connector shown in FIG. 8, in accordance with the first exemplary embodiment of the present invention.

FIG. 8 is a front view of a first exemplary latch connector 18 for the modular component sterilization system 10 shown in FIG. 1, in accordance with the first exemplary embodiment of the present invention. FIG. 9 is a side view of the first exemplary latch connector 18 shown in FIG. 8, in accordance with the first exemplary embodiment of the present invention. The latch connector 18 may include at least one latch connector element 36. The latch connector element 36 may be a flexible tabs having a latch cylindrical protrusion 38. The latch cylindrical protrusion 38 may be sized to be received by the openings 26 and/or slots 28 of the case walls 12,12A shown in FIG. 2 and FIG. 3. The latch connector 18 may also include at least one pair of latch bracing elements 40. The pair of latch bracing elements 40 may be substantially parallel, as shown in FIG. 9, and spaced a distance S exceeding a thickness of the case walls 12, 12A (shown in FIG. 2 and FIG. 3). The latch bracing elements 40 may be located about a periphery of the latch connector element 36. The latch connector element 36 may be coplanar with a first bracing element 40A of the pair of bracing elements 40 and the cylindrical latch protrusion 38 may extend from the latch connector element 36 toward the second latch bracing element 40B of the pair of latch bracing elements 40.

Operationally, a case wall 12, 12A may be slid between the pair of latch bracing elements 40 so that the cylindrical latch protrusion 38 contacts the case wall 12, 12A and the latch connector element 36 flexes away from the second latch bracing element 40B. The flexing of the latch connector element 36 allows the case wall 12,12A to slide further between the pair of latch bracing elements 40 such that the cylindrical latch protrusion 38 on the latch connector element 36 engages with the openings 26 and/or slots 28. The cylindrical latch protrusion 38 may be beveled to further enable the latch connector element 36 to flex away from the second latch bracing element 40B on contact from the case wall 12, 12A, but limit flexing when a pulling force is exerted between the latch connector 18 and the case wall 12, 12A. To remove the case wall 12, 12A, the cylindrical latch protrusion 38 may be pushed from the opening 26 and/or slots 28 to disengage the latch connector element 36.

The latch connector 18 also includes a latch mechanism 42. The latch mechanism 42 includes a latch frame 44 integral with the pair of latch bracing elements 40. A latch 46 is pivotable with the latch frame 44 at a proximal end of the latch 46. A latch cylindrical protrusion 48 is integral with the latch 46 at a distal end of the latch 46. The latch connector 18 may be useful for allowing one case wall 12, 12A to operate as a cover for the modular component sterilization system 10.

Specifically, the cover may be connected to a plurality of latch connectors 18 through the respective latch connector elements 36. The respective latch mechanisms 42 may then be used to connect the cover to the rest of an open container built with the modular component sterilization system 10. The latch connector 18 allows for an easier engagement/disengagement of a cover than the connectors 14, 14A. When in a closed position, the latch 46 should be biased, frictionally or otherwise, from moving into an open position. Biasing the latch 46 limits the possibility the cover becomes unintentionally disengaged from the rest of the container. Those having ordinary skill in the art will recognize that a variety of other latching designs are known in the art may be used in the place of the latch mechanism 42 herein, and such latching designs are considered to be within the scope of the present invention.

Figure 11:
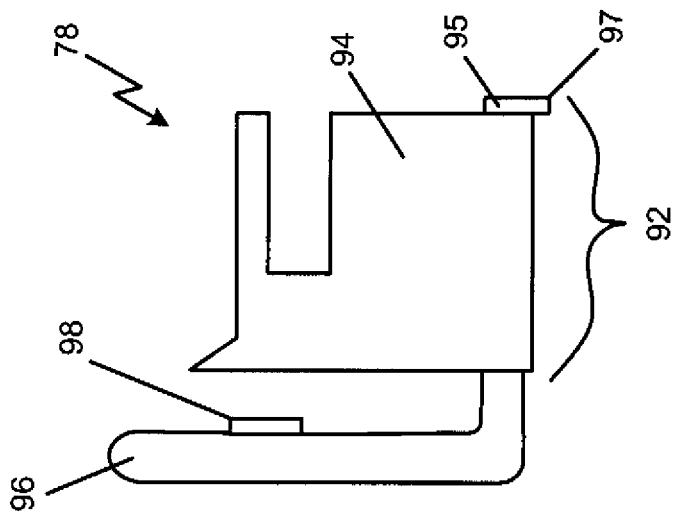
FIG. 11 is another side view of the second exemplary latch connector shown in FIG. 10, in accordance with the first exemplary embodiment of the present invention.
Figure 10:
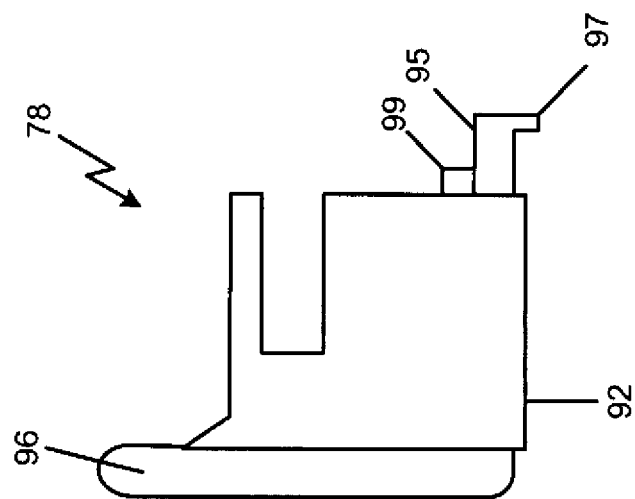
FIG. 10 is a side view of a second exemplary latch connector for the modular component sterilization system shown in FIG. 1, in accordance with the first exemplary embodiment of the present invention.

FIG. 10 is a side view of a first exemplary latch connector 78 shown in FIG. 1 in a closed position, in accordance with the first exemplary embodiment of the present invention. FIG. 11 is a side view of the first exemplary latch connector 78 shown in FIG. 10 in an open position, in accordance with the first exemplary embodiment of the present invention. The latch connector 78 of FIG. 10 and FIG. 11 is similar to the latch connector 18 of FIG. 8 and FIG. 9, but differs in that latch connector 78 is slidable, whereas latch connector 18 is pivotable. The latch connector 78 may include at least one latch connector element 96. The latch connector element 96 may be flexible tabs having a latch cylindrical protrusion 98. The latch cylindrical protrusion 98 may be sized to be received by the openings 26 and/or slots 28 of the case walls 12, 12A shown in FIG. 2 and FIG. 3.

Operationally, a case wall 12, 12A may be slid to abut latch element 96 so that the cylindrical latch protrusion 98 contacts the case wall 12, 12A and the latch connector element 96 flexes to allow the case wall 12, 12A to slide in to an engaging position between the cylindrical latch protrusion 98 on the latch connector element 96 and the openings 26 and/or slots 28. The cylindrical latch protrusion 98 may be beveled to further enable the latch connector element 96 to flex upon on contact with the case wall 12, 12A, but limit flexing when a pulling force is exerted between the latch connector 78 and the case wall 12, 12A. To remove the case wall 12, 12A, the cylindrical latch protrusion 98 may be pushed from the opening 26 and/or slots 28 to disengage the latch connector element 96.

The latch connector 78 also includes a latch mechanism 92. The latch mechanism 92 includes a latch frame 94. A latch 95 is slidable with the latch frame 94 at a proximal end of the latch 95. A latch cylindrical protrusion 99 is integral with the latch 95 at a distal end of the latch 95. The latch connector 78 may be useful for allowing one case wall 12, 12A to operate as a cover for the modular component sterilization system 10.

Specifically, the cover may be connected to a plurality of latch connectors 78 through the respective latch connector elements 96. The respective latch mechanisms 92 may then be used to connect the cover to the rest of an open container built with the modular component sterilization system 10. The latch connector 78 allows for an easier engagement/disengagement of a cover than the connectors 14, 14A. The latch 95 includes a latch stop 97 to prevent the latch frame 94 from separating from entirely from the latch 95. Those having ordinary skill in the art will recognize that a variety of other latching designs are known in the art may be used in the place of the latch mechanism 92 herein, and such latching designs are considered to be within the scope of the present invention.

Figure 12:
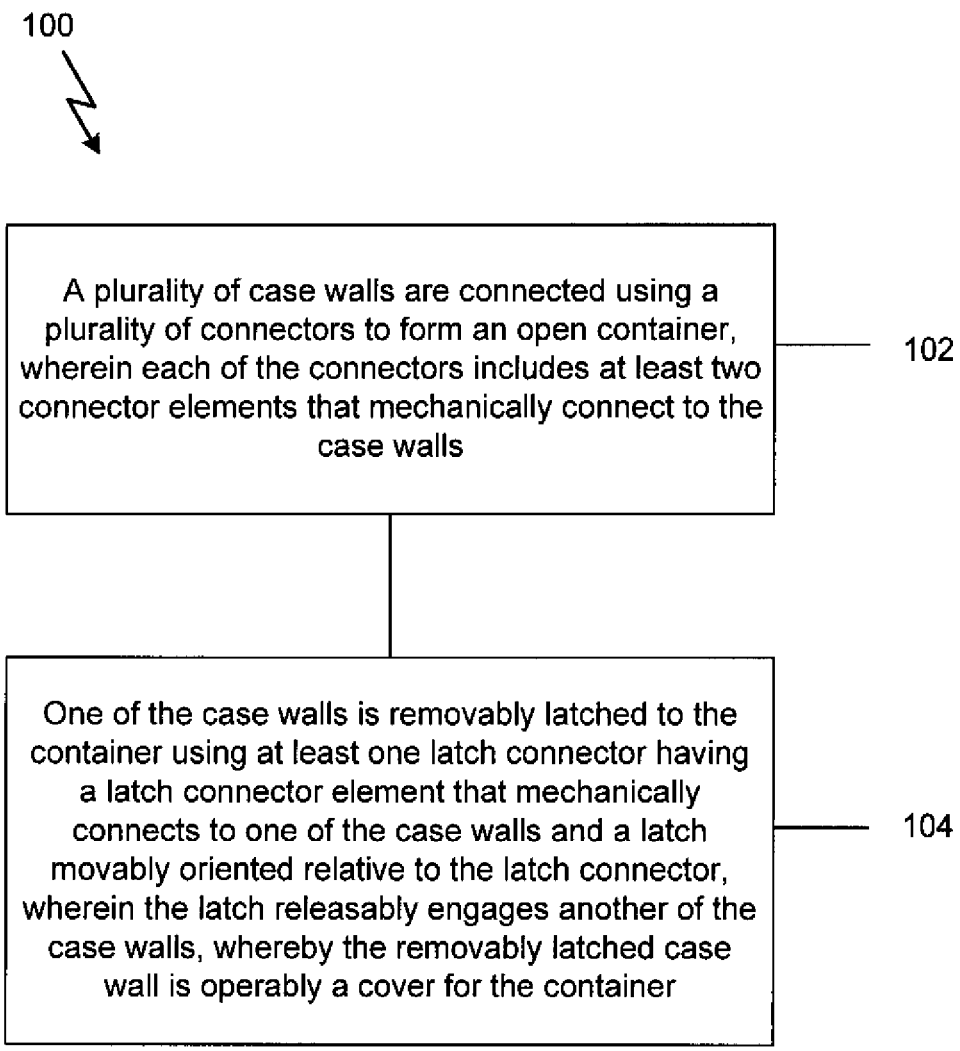
FIG. 12 is a flowchart illustrating a method of utilizing the modular component sterilization system of FIG. 1, in accordance with the first exemplary embodiment of the present invention.

FIG. 12 is a flowchart 100 illustrating a method of utilizing the abovementioned modular component sterilization system 10 in accordance with the first exemplary embodiment of the invention. It should be noted that any process descriptions or blocks in flow charts should be understood as representing modules, segments, portions of code, or steps that include one or more instructions for implementing specific logical functions in the process, and alternate implementations are included within the scope of the present invention in which functions may be executed out of order from that shown or discussed, including substantially concurrently or in reverse order, depending on the functionality involved, as would be understood by those reasonably skilled in the art of the present invention.

As is shown by block 102, a plurality of case walls 12, 12A are connected using a plurality of connectors 14, 14A to form an open container, wherein each of the connectors 14, 14A includes at least two connector elements 16 that mechanically connect to the case walls 12, 12A. One of the case walls 12, 12A is removably latched to the container using at least one latch connector 18 having a latch connector element 36 that mechanically connects to one of the case walls 12, 12A and a latch 46 movably oriented relative to the latch connector 36, wherein the latch 46 releasably engages another of the case walls 12, 12A, whereby the removably latched case wall 12, 12A is operably a cover for the container (block 104).

Additionally, the method of using the modular component sterilization system 10 may include the step of replacing a component or part of the system, including the latch 46, 95, the case walls 12, 12A, or any other feature of the system 10, without replacing the entire system 10. For example, if a latch 46, 95 were to break or become worn out, a new latch 46, 95 may be installed within the system 10 for repair. Furthermore, it is noted that the replacement of parts may be accomplished within the working environment, and thus, the system 10 would not need to be returned to a factory or manufacturer for repair.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A system for a modular component sterilization case, the system comprising:
    a plurality of case walls, each case wall having a plurality of through-holes, wherein each of the plurality of through-holes is formed through an entire thickness of each case wall, respectively;
    a plurality of connectors, each having at least two connector elements, and at least one bracing element for each of the at least two connector elements, wherein the at least one bracing element is positioned a spaced distance from at least one of the at least two connector elements, wherein a gap is formed between the at least one bracing element and the at least one of the at least two connector elements, and wherein at least one of the plurality of case walls is removably insertable within the gap;
    at least one protrusion element connected to each of the at least two connector elements, wherein the at least one protrusion element is flexibly movable within the gap, and wherein the at least one protrusion element engages with one of the plurality of through-holes within at least one of the plurality of case walls when it is positioned within the gap; and
    at least one latch connector having at least one latch connector element that mechanically connects to one of the plurality of through-holes within at least one of the case walls and a latch connected to the at least one latch connector element, wherein the latch is movable relative to the latch connector element, wherein the latch releasably engages another of the case walls, and wherein the latch is pivotally connected to the latch connector element.

2. The system of claim 1, further comprising a plurality of corner connectors, wherein each of the corner connectors includes at least three connector elements that mechanically connect to the case walls, wherein the case walls are not coplanar.

3. The system of claim 1, wherein one of the plurality of case walls is a cover and one of the latch and the latch connector element engages the cover.

4. The system of claim 1, wherein the connectors connect at least two case walls at approximate right angles.

5. The system of claim 1, further comprising at least one slot formed through an entire thickness of the case walls wherein the at least one protrusion element on each of the connector elements is received within the at least one slot when the case walls are positioned within the gap.

6. The system of claim 1, wherein the at least one bracing element for each of the at least two connector elements further comprises a pair of bracing elements for each of the at least two connector elements, wherein a first bracing element of the pair of bracing elements is located about a periphery of one of the connector elements, wherein the gap is positioned between the pair of bracing elements, and wherein one of the case walls is received within the gap between the pair of bracing elements.

7. The system of claim 6, wherein the first bracing element of the pair of bracing elements is substantially coplanar with one of the connector elements.

8. The system of claim 1, wherein each of the through-holes further comprise at least one opening formed in the case walls, wherein the protrusion elements on each of the connector elements further comprise a cylindrical protrusion received by the at least one opening when at least one of the case walls is positioned within the gap.

9. The system of claim 1, further comprising a plurality of fluid permeable holes within at least one of the plurality of walls.

10. The system of claim 1, wherein each of the at least two connector elements is integrally fixed to one of the plurality of connectors.

11. A system for a modular component sterilization case, the system comprising:
    a plurality of case walls, each case wall having a plurality of through-holes, wherein each of the plurality of through-holes is formed through an entire thickness of each case wall, respectively;
    a plurality of connectors, each having at least two connector elements, and at least one bracing element for each of the at least two connector elements, wherein the at least one bracing element is positioned a spaced distance from at least one of the at least two connector elements, wherein a gap is formed between the at least one bracing element and the at least one of the at least two connector elements, and wherein at least one of the plurality of case walls is removably insertable within the gap;
    at least one protrusion element connected to each of the at least two connector elements, wherein the at least one protrusion element is flexibly movable within the gap, and wherein the at least one protrusion element engages with one of the plurality of through-holes within at least one of the plurality of case walls when it is positioned within the gap; and at least one latch connector having at least one latch connector element that mechanically connects to one of the plurality of through-holes within at least one of the case walls and a latch connected to the at least one latch connector element, wherein the latch is movable relative to the latch connector element, wherein the latch releasably engages another of the case walls, wherein the at least one latch connector element of the latch connector further comprises a connector element and at least one bracing element, wherein the at least one bracing element is positioned a spaced distance from the connector element, wherein a gap is formed between the at least one bracing element and the connector element, and wherein at least one of the plurality of case walls is removably insertable within the gap.

* * * * *